(12) United States Patent
Riazuddin et al.

(10) Patent No.: US 8,809,354 B2
(45) Date of Patent: Aug. 19, 2014

(54) 3-AMINO-2-(4-NITROPHENYL)-4-(3H)-QUINAZOLINONE OR DERIVATIVES THEREOF FOR TREATING OR PREVENTING ANTIVIRAL INFECTIONS

(76) Inventors: Sheikh Riazuddin, Lahore (PK); Osman Ali, Tat Lahore (PK); Usman Ashfaq, Lahore (PK); Shaheen N. Khan, Lahore (PK); Javed Akram, Lahore (PK); Atta-ur Rahman, Karachi (PK); M. Iqbal Choudhary, Karachi (PK); Khalid M. Khan, Karachi (PK); Zulfiqar Ali Khan, Karachi (PK)

( * ) Notice: Subject to any disclaimer, the term of this patent is extended or adjusted under 35 U.S.C. 154(b) by 168 days.

(21) Appl. No.: 13/341,989

(22) Filed: Dec. 31, 2011

(65) Prior Publication Data

US 2013/0171101 A1 Jul. 4, 2013

(51) Int. Cl.
*A01N 43/54* (2006.01)
*A61K 31/517* (2006.01)
*C07D 239/72* (2006.01)

(52) U.S. Cl.
USPC ............ 514/266.1; 514/266.2; 544/283; 544/284; 544/289

(58) Field of Classification Search
USPC ............ 514/266.1, 266.2; 544/283, 284, 287
See application file for complete search history.

(56) References Cited

U.S. PATENT DOCUMENTS

| | | | |
|---|---|---|---|
| 3,375,250 A * | 3/1968 | Kirchner et al. | 544/287 |
| 3,843,654 A * | 10/1974 | Kirchner et al. | 544/231 |
| 5,026,687 A | 6/1991 | Yarchoan et al. | |
| 5,372,808 A | 12/1994 | Blatt et al. | |
| 5,491,135 A | 2/1996 | Blough | |
| 5,496,546 A | 3/1996 | Wang et al. | |
| 5,538,865 A | 7/1996 | Reyes et al. | |
| 5,610,054 A | 3/1997 | Draper | |
| 5,633,358 A | 5/1997 | Gruetzke et al. | |
| 5,663,388 A | 9/1997 | Vargas et al. | |
| 5,676,942 A | 10/1997 | Testa et al. | |
| 5,725,859 A | 3/1998 | Omer | |
| 5,738,845 A | 4/1998 | Imakawa | |
| 5,830,455 A | 11/1998 | Valtuena et al. | |
| 5,830,905 A | 11/1998 | Diana et al. | |
| 5,837,257 A | 11/1998 | Tsai et al. | |
| 5,846,964 A | 12/1998 | Ozeki | |
| 5,849,696 A | 12/1998 | Chretien et al. | |
| 5,849,800 A | 12/1998 | Smith | |
| 5,858,389 A | 1/1999 | Elsherbini | |
| 5,869,253 A | 2/1999 | Draper | |
| 5,891,874 A | 4/1999 | Colacino et al. | |
| 5,908,621 A | 6/1999 | Glue et al. | |
| 5,922,757 A | 7/1999 | Chojkier | |
| 5,922,857 A | 7/1999 | Han et al. | |
| 5,928,636 A | 7/1999 | Alber et al. | |
| 5,942,223 A | 8/1999 | Bazer et al. | |
| 5,969,109 A | 10/1999 | Bona et al. | |
| 5,972,347 A | 10/1999 | Eder et al. | |
| 5,980,884 A | 11/1999 | Blatt et al. | |
| 5,990,276 A | 11/1999 | Zhang et al. | |
| 6,001,799 A | 12/1999 | Chretien et al. | |
| 6,001,990 A | 12/1999 | Wands et al. | |
| 6,004,933 A | 12/1999 | Spruce et al. | |
| 6,030,960 A | 2/2000 | Morris-Natschke et al. | |
| 6,034,134 A | 3/2000 | Gold et al. | |
| 6,043,077 A | 3/2000 | Barber et al. | |
| 6,056,961 A | 5/2000 | Lavie et al. | |

FOREIGN PATENT DOCUMENTS

| | | |
|---|---|---|
| DE | 19914474 A1 | 10/1999 |
| JP | 10101591 | 10/1998 |
| WO | 97/36554 A1 | 10/1997 |
| WO | 98/17679 A1 | 4/1998 |
| WO | 99/07734 A2 | 2/1999 |

* cited by examiner

*Primary Examiner* — Paul V. Ward
(74) *Attorney, Agent, or Firm* — Safaraz K. Niazi

(57) ABSTRACT

Surprising antiviral activity of 3-amino-2-(4-nitrophenyl)-4-(3H)-quinazolinone (Compound 1) was reported in the treatment or prevention of viral infections, particularly in combination with other antiviral agents such as interferon and/or ribavarin.

4 Claims, 4 Drawing Sheets

3-amino-2-(4-nitrophenyl)-4-(3H)-quinazolinone

3-AMINO-2-(4-NITROPHENYL)-4-(3H)-QUINAZOLINONE OR DERIVATIVES THEREOF FOR TREATING OR PREVENTING ANTIVIRAL INFECTIONS

BACKGROUND OF THE INVENTION

The hepatitis C virus (HCV) is the leading cause of chronic liver disease worldwide (Boyer, N. et al. J. Hepatol. 32:98-112, 2000). HCV causes a slow growing viral infection and is the major cause of cirrhosis and hepatocellular carcinoma (Di Besceglie, A. M. and Bacon, B. R., Scientific American, October: 80-85, (1999); Boyer, N. et al. J. Hepatol. 32:98-112, 2000). An estimated 170 million persons are infected with HCV worldwide (Boyer, N. et al. J. Hepatol. 32:98-112, 2000). Cirrhosis caused by chronic hepatitis C infection accounts for 8,000-12,000 deaths per year in the United States, and HCV infection is the leading indication for liver transplant. In many parts of the world, specially, the Third World, the hepatitis C positive population may comprise as high as 9-10% increasing the total population affected by hepatitis C well in excess of 300 Million.

HCV is known to cause at least 80% of post-transfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear (The Merck Manual, ch. 69, p. 901, 16th ed., (1992)).

HCV has been classified as a member of the virus family Flaviviridae that includes the genera flaviviruses, pestiviruses, and hapaceiviruses, which includes hepatitis C virus (Rice, C. M., Flaviviridae: The viruses and their replication. In: Fields Virology, Editors: Fields, B. N., Knipe, D. M., and Howley, P. M., Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

A significant focus of current antiviral research is directed toward the development of improved methods of treatment of chronic HCV infections in humans (Di Besceglie, A. M. and Bacon, B. R., Scientific American, October: 80-85, (1999)). Currently, there are two primary antiviral compounds, ribavirin and interferon-alpha, which are used for the treatment of chronic HCV infections in humans.

Treatment of HCV Infection with Ribivarin

Ribavirin (1-β-D-ribofuranosyl-1-1,2,4-triazole-3-carboxamide) is a synthetic, non-interferon-inducing, broad spectrum antiviral nucleoside analog sold under the trade name, Virazole (The Merck Index, 11th edition, Editor: Budavari, S., Merck & Co., Inc., Rahway, N.J., p 1304, 1989). U.S. Pat. Nos. 3,798,209 and RE29,835 disclose and claim Ribavirin. Ribavirin is structurally similar to guanosine, and has in vitro activity against several DNA and RNA viruses including Flaviviridae (Gary L. Davis. Gastroenterology 118:S104-S114, 2000).

Ribavirin reduces serum amino transferase levels to normal in 40% or patients, but it does not lower serum levels of HCV-RNA (Gary L. Davis. Gastroenterology 118:S104-S114, 2000). Thus, Ribavirin alone is not effective in reducing viral RNA levels. Additionally, Ribavirin has significant toxicity and is known to induce anemia.

Treatment of HCV Infection with Interferon

Interferons (IFNs) are compounds that have been commercially available for the treatment of chronic hepatitis for nearly a decade. IFNs are glycoproteins produced by immune cells in response to viral infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Gary L. Davis. Gastroenterology 118:S104-S114, 2000).

A number of patents disclose HCV treatments using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,908,621 to Glue et al. discloses the use of polyethylene glycol modified interferon for the treatment of HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al, U.S. Pat. No. 5,372,808 to Blatt et al., and U.S. Pat. No. 5,849,696.

Combination of Interferon and Ribavirin

The combination of IFN and Ribavirin for the treatment of HCV infection has been reported to be effective in the treatment of IFN naive patients (Battaglia, A. M. et al., Ann. Pharmacother. 34:487-494, 2000). Results are promising for this combination treatment both before hepatitis develops or when histological disease is present (Berenguer, M. et al. Antivir. Ther. 3(Suppl. 3):125-136, 1998). Side effects of combination therapy include hemolysis, flu-like symptoms, anemia, and fatigue. (Gary L. Davis. Gastroenterology 118: S104-S114, 2000).

Additional References Disclosing Methods to Treat HCV Infections

A number of HCV treatments are reviewed by Bymock et al. in Antiviral Chemistry & Chemotherapy, 11:2; 79-95 (2000). Several substrate-based NS3 protease inhibitors have been identified in the literature, in which the scissile amide bond of a cleaved substrate is replaced by an electrophile, which interacts with the catalytic serine. Attwood et al. (1998) Antiviral peptide derivatives, 98/22496; Attwood et al. (1999), Antiviral Chemistry and Chemotherapy 10.259-273; Attwood et al. (1999) Preparation and use of amino acid derivatives as anti-viral agents, German Patent Publication DE 19914474; Tung et al. (1998) Inhibitors of serine proteases, particularly hepatitis C virus NS3 protease, WO 98/17679. The reported inhibitors terminate in an electrophile such as a boronic acid or phosphonate. Llinas-Brunet et al. (1999) Hepatitis C inhibitor peptide analogues, WO 99/07734. Two classes of electrophile-based inhibitors have been described, alphaketoamides and hydrazinoureas.

The literature has also described a number of non-substrate-based inhibitors. For example, evaluation of the inhibitory effects of 2,4,6-trihydroxy-3-nitro-benzamide derivatives against HCV protease and other serine proteases has been reported. Sudo, K. et al., (1997) Biochemical and Biophysical Research Communications, 238:643-647; Sudo, K. et al. (1998) Antiviral Chemistry and Chemotherapy 9:186. Using a reverse-phase HPLC assay, the two most potent compounds identified were RD3-4082 and RD3-4078, the former substituted on the amide with a 14-carbon chain and the latter processing a para-phenoxyphenyl group.

Thiazolidine derivatives have been identified as micromolar inhibitors, using a reverse-phase HPLC assay with an NS3/4A fusion protein and NS5A/5B substrate. Sudo, K. et al. (1996) Antiviral Research 32:9-18. Compound RD-1-6250, possessing a fused cinnamoyl moiety substituted with a long alkyl chain, was the most potent against the isolated enzyme. Two other active examples were RD4 6205 and RD4 6193.

Other literature reports screening of a relatively small library using an ELISA assay and the identification of three compounds as potent inhibitors, a thiazolidine and two benzanilides. Kakiuchi N. et al. J. EBS Letters 421:217-220; Takeshita N. et al., Analytical Biochemistry 247:242-246, 1997. Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al.

Isolated from the fermentation culture broth of *Streptomyces* sp., Sch 68631, a phenan-threnequinone, possessed micromolar activity against HCV protease in a SDS-PAGE and autoradiography assay. Chu M. et al., Tetrahedron Letters 37:7229-7232, 1996. In another example by the same authors, Sch 351633, isolated from the fungus *Penicillium griscofuluum*, demonstrated micromolar activity in a scintillation proximity assay. Chu M. et al., Bioorganic and Medicinal Chemistry Letters 9:1949-1952. Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, .alpha.-chymotrypsin, chymase and subtilisin. Qasim M. A. et al., Biochemistry 36:1598-1607, 1997.

HCV helicase inhibitors have also been reported. U.S. Pat. No. 5,633,358 to Diana G. D. et al.; PCT Publication No. WO 97/36554 of Diana G. D. et al. There are a few reports of HCV polymerase inhibitors: some nucleotide analogues, gliotoxin and the natural product cerulenin. Ferrari R. et al., Journal of Virology 73:1649-1654, 1999; Lohmann V. et al., Virology 249:108-118, 1998.

Antisense phosphorothioate oligodeoxynucleotides complementary to sequence stretches in the 5' non-coding region of the HCV, are reported as efficient inhibitors of HCV gene expression in in vitro translation and IIcpG2 IICV-luciferase cell culture systems. Alt M. et al., Hepatology 22:707-717, 1995. Recent work has demonstrated that nucleotides 326-348 comprising the 3' end of the NCR and nucleotides 371-388 located in the core-coding region of the HCV RNA are effective targets for antisense-mediated inhibition of viral translation. Alt M. et al., Archives of Virology 142:589-599, 1997. U.S. Pat. No. 6,001,990 to Wands et al. discloses oligonucleotides for inhibiting the replication of HCV. PCT Publication No. WO 99/29350 discloses compositions and methods of treatment for hepatitis C infection comprising the administration of antisense oligonucleotides that are complementary and hybridizable to HCV-RNA.

U.S. Pat. No. 5,922,857 to Han et al. disclose nucleic acids corresponding to the sequence of the pestivirus homology box IV area for controlling the translation of HCV. Antisense oligonucleotides as therapeutic agents have been recently reviewed (Galderisi U. et al., Journal of Cellular Physiology 181:251-257, 1999).

Other compounds have been reported as inhibitors of IRES-dependent translation in HCV. Japanese Patent Publication JP-08268890 of Ikeda N et al.; Japanese Patent Publication JP-10101591 of Kai, Y. et al. Nuclease-resistant ribozymes have been targeted at the IRES and recently reported as inhibitors in an HCV-poliovirus chimera plaque assay. Maccjak D. J. et al., Hepatology 30 abstract 995, 1999. The use of ribozymes to treat HCV is also disclosed in U.S. Pat. No. 6,043,077 to Barber et al., and U.S. Pat. Nos. 5,869, 253 and 5,610,054 to Draper et al.

Other patents disclose the use of immune system potentiating compounds for the treatment of HCV. For example, U.S. Pat. No. 6,001,799 to Chretien et al. discloses a method of treating hepatitis C in non-responders to interferon treatment by administering an immune system potentiating dose of thymosin or a thymosin fragment. U.S. Pat. No. 5,972,347 to Eder et al. and U.S. Pat. No. 5,969,109 to Bona et al. disclose antibody-based treatments for treating HCV.

U.S. Pat. No. 6,034,134 to Gold et al. discloses certain NMDA receptor agonists having immunodulatory, antimalarial, anti-Borna virus and anti-Hepatitis C activities. The disclosed NMDA receptor agonists belong to a family of 1-amino-alkylcyclohexanes. U.S. Pat. No. 6,030,960 to Morris-Natscke et al. discloses the use of certain alkyl lipids to inhibit the production of hepatitis-induced antigens, including those produced by the HCV virus. U.S. Pat. No. 5,922,757 to Chojkier et al. discloses the use of vitamin E and other antioxidants to treat hepatic disorders including HCV. U.S. Pat. No. 5,858,389 to Elsherbi et al., discloses the use of squalene for treating hepatitis C. U.S. Pat. No. 5,849,800 to Smith et al discloses the use of amantadine for treatment of Hepatitis C. U.S. Pat. No. 5,846,964 to Ozeki et al. discloses the use of bile acids for treating HCV. U.S. Pat. No. 5,491,135 to Blough et al. discloses the use of N-(phosphonoacetyl)-L-aspartic acid to treat flaviviruses such as HCV.

Other compounds proposed for treating HCV include plant extracts (U.S. Pat. No. 5,837,257 to Tsai et al., U.S. Pat. No. 5,725,859 to Omer et al., and U.S. Pat. No. 6,056,961), piperidenes (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.).

In light of the fact that the hepatitis C virus has reached epidemic levels worldwide, and has tragic effects on the infected patient, there remains a strong need to provide new effective pharmaceutical agents to treat hepatitis C that has low toxicity to the host.

Therefore, it is an object of the present invention to provide a compound, method and composition for the treatment of a host infected with hepatitis C virus.

SUMMARY OF THE INVENTION

Compounds, methods and compositions for the treatment of hepatitis C infection are described that include an effective hepatitis C treatment amount of Compound 1, or a pharmaceutically acceptable salt or prodrug thereof.

In a first principal embodiment, a compound of Formula I, or a pharmaceutically acceptable salt or prodrug thereof, is provided.

DETAILED DESCRIPTION OF THE INVENTION

Figure 1:
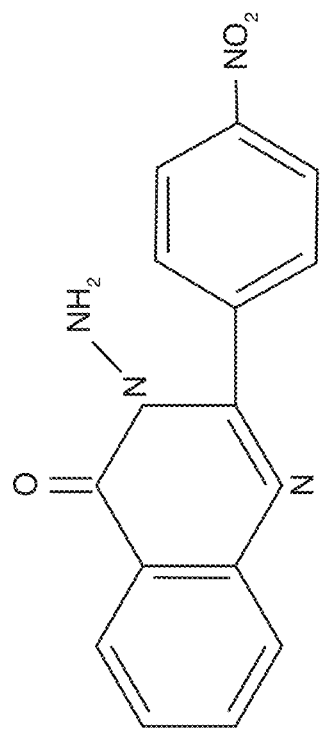
FIG. 1 provides the structure of Compound 1.

The invention as disclosed herein is a compound, method and composition for the treatment of hepatitis C in humans or other host animals, that includes administering an effective HCV treatment amount of Compound 1 as described herein or a pharmaceutically acceptable salt or prodrug thereof, optionally in a pharmaceutically acceptable carrier. The compounds of this invention either possess antiviral (i.e., anti-HCV) activity, or are metabolized to a compound that exhibits such activity. Compound 1 is a synthetic compound belonging to the quinazolinone class of compounds. Its chemical structure is elucidated in FIG. 1.

FIG. 1

Figure 2:
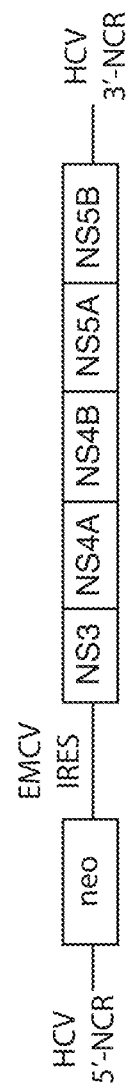
FIG. 2 is genetic organization of the HCV sub-genomic replicon

FCA-4 sub genomic replicon was bicistronic construct composed of the HCV IRES (nucleotides 1 to 377 of the 5'NCR); the neomycin phosphotransferase (neo) gene; the encephalomyocarditis IRES, which mediates the translation of HCV nonstructural proteins NS3 through NS5; and the 3'NCR as shown in FIG. 2. HCV replicons do not contain structural proteins and NS2 because they are probably not needed for replication of HCV RNA. FCA-4 sub-genomic replicon consists of single adaptive mutation and a deletion of a serine residue at position 1176 (Guo et al, 2001). Cells were maintained in G418-containing medium in a sub-confluent state to ensure optimal cell growth and hence efficient replicon replication. FIG. 2 shows genetic organization of the HCV sub-genomic replicon.

FIG. 2

The bicistronic RNA molecule contains the HCV IRES and a few core-coding sequences, which are followed by neomycin phosphotransferase gene (Neor). These sequences are followed by the encephalomyocarditis virus IRES placed in front of HCV sequences encoding nonstructural protein NS3 to NS5B, terminating at the HCV 3NCR.

To determine the antiviral effect against HCV, FCA 4 cells were seeded in six well plates. After 24 h, media containing 20 µM of test compound was added to the plates. Cells were incubated at 37° C. in CO2 incubator for additional 48 h. At the end of the incubation, cells were harvested, RNA was extracted and cDNA were generated by oligo dT priming. cDNA was amplified by PCR using primers specific to the 5'UTR and NS5B gene of HCV. Amplification of GAPDH mRNA served as an internal control. It was demonstrated that Compound 1 inhibited HCV RNA expression significantly at a concentration of 20 µM, while GAPDH mRNA expression remains unaffected by the addition of the Compound 1. The antiviral suppression mediated by Compound 1 is independent of cytotoxicity. After antiviral analysis, Compound 1 was docked with hepatitis C virus RNA-directed RNA polymerase (NS5B), Serine protease/NTPase/helicase (NS3), Interferon-induced double-stranded RNA-activated protein kinase (PKR) (Uniprot accession No: P19525), Signal transducer and activator of transcription 1-alpha/beta (STAT1) (Uniprot accession No: P42224) and Suppressor of cytokine signaling 3 (SOCS 3). Auto-Dock program was used to identify ligands binding to NS5b, NS3 and host genes. Auto-Dock is a suite of automated docking tools, which is designed to predict binding of small molecules, such as drugs or substrates, to a receptor of known 3D structure. Our data showed that the most important interaction is the binding of Compound 1 with HCV NS5b. Compound 1 formed H-bonds with NS5B. The residues which showed interaction with the ligands include Lys 141, Asp 225, Thr 287, Asn 291, Cys 316, Asp 318, Cys 366, Ser 368, Arg 386, Asn 411, Tyr 415 and Tyr 448. These residues played an important role in initiation and elongation step.

In Compound 1 nitrogen at position 1 and oxygen at position 3 each accepts hydrogen from Asn411 and Thr287 respectively, whereas 7-nitro group forms hydrogen bonds with both Lys141 and Arg386 (Table 1).

The amino group at position 3 donates hydrogen bond to all of the residues interacting with Compound 1 (Table 1).

TABLE 1

| Compound 1 conformation interacting with NS5B | | |
|---|---|---|
| Conformation | Residue | Binding energy |
| 2_1 | Asp 318 | −6.4 |
| 2_2 | Asp 318 | −6.4 |
| 2_3 | Asp 318 | −6.39 |
| 2_4 | Asp 318 | −6.39 |
| 2_5 | Asp 318 | −6.35 |
| 3_1 | Ser 368 | −6.27 |
| 3_2 | Ser 368, Tyr 448 | −6.26 |
| 3_3 | Tyr 448 | −6.13 |
| 4_1 | Cys 366, Asn 411, Tyr 415 | −6.08 |

Figure 3:
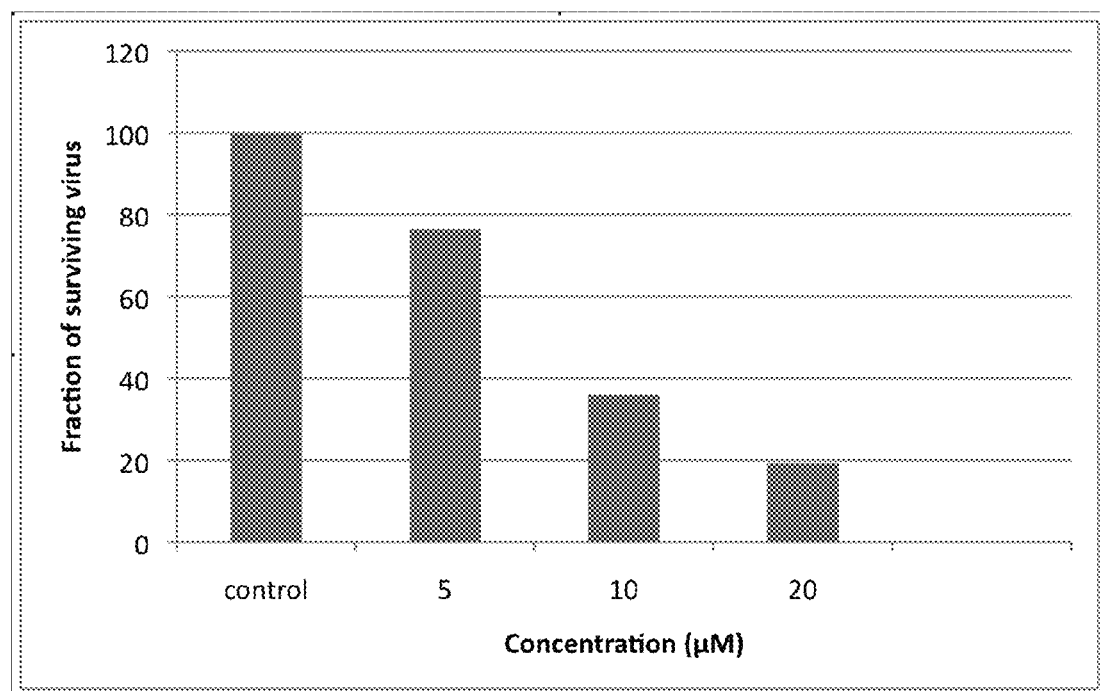
FIG. 3 is a bar graph of the dose response of Compound 1 against HCV 3a genotype.

Dose-dependent studies on the activity of Compound 1 in Huh-7 cells were conducted where Huh 7 cells were infected with $2 \times 10^5$ copies of HCV 3a genotype per well in the absence and presence of different concentrations of Compound 1. After 24 hrs incubation period, total RNA was extracted by Gentra kit, and the levels of HCV RNA remaining were determined, by real time Quantitative RT-PCR assay and are shown as percentage of HCV RNA survival in cells. Results are represented in FIG. 3 as the average and standard error for three independent experiments. FIG. 3 shows a dose response of Compound 1 against HCV 3a genotype.

FIG. 3

In summary, the present invention includes the following features:

(a) Compound 1, as described herein, and pharmaceutically acceptable salts and prodrugs thereof;

(b) Compound 1 as described herein, and pharmaceutically acceptable salts and prodrugs thereof for use in the treatment or prophylaxis of an HCV infection, especially in individuals diagnosed as having an HCV infection or being at risk for becoming infected by HCV;

(c) Use of Compound 1, and pharmaceutically acceptable salts and prodrugs thereof in the manufacture of a medicament for treatment of an HCV infection;

(d) pharmaceutical formulations comprising the Compound 1 or pharmaceutically acceptable salts or prodrugs thereof together with a pharmaceutically acceptable carrier or diluent;

The active Compound 1 can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts." Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

Combination and Alternation Therapy

It has been recognized that drug-resistant variants of HCV can emerge after prolonged treatment with an antiviral agent. Drug resistance most typically occurs by mutation of a gene that encodes for an enzyme used in viral replication. The efficacy of a drug against HCV infection can be prolonged, augmented, or restored by administering the Compound 1 in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Non-limiting examples of antiviral agents that can be used in combination with the compounds disclosed herein include:

(1) an interferon and/or ribavirin (Battaglia, A. M. et al., Ann. Pharmacother. 34:487-494, 2000); Berenguer, M. et al. Antivir. Ther. 3(Suppl. 3):125-136, 1998);

(2) Substrate-based NS3 protease inhibitors (Attwood et al., Antiviral peptide derivatives, PCT WO 98/22496, 1998; Attwood et al., Antiviral Chemistry and Chemotherapy 10.259-273, 1999; Attwood et al., Preparation and use of amino acid derivatives as anti-viral agents, German Patent Publication DE 19914474; Tung et al Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate. Llinas-Brunet et al, Hepatitis C inhibitor peptide analogues, PCT WO 99/07734.

Non-substrate-based inhibitors such as 2,4,6-trihydroxy-3-nitro-benzamide derivatives (Sudo K. et al., Biochemical and Biophysical Research Communications, 238:643-647, 1997; Sudo K. et al. Antiviral Chemistry and Chemotherapy 9:186, 1998), including RD3-4082 and RD3-4078, the former substituted on the amide with a 14-carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., Antiviral Research 32:9-18, 1996), especially compound RD-1-6250, possessing a fused cinnamoyl moiety substituted with a long alkyl chain, RD4 6205 and RD4 6193;

(5) Thiazolidines and benzanilides identified in Kakiuchi N. et al. J. EBS Letters 421:217-220; Takeshita N. et al. Analytical Biochemistry 247:242-246, 1997;

(6) A phenan-threnequinone possessing activity against HCV protease in a SDS-PAGE and autoradiography assay isolated from the fermentation culture broth of *Streptomyces* sp., Sch 68631 (Chu M. et al., Tetrahedron Letters 37:7229-7232, 1996), and Sch 351633, isolated from the fungus *Penicillium griscofuluum*, which demonstrates activity in a scintillation proximity assay (Chu M. et al., Bioorganic and Medicinal Chemistry Letters 9:1949-1952);

(7) Selective NS3 inhibitors based on the macromolecule elgin c, isolated from leech (Qasim M. A. et al., Biochemistry 36:1598-1607, 1997);

(8) HCV helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(9) HCV polymerase inhibitors such as nucleotide analogues, gliotoxin (Ferrari R. et al. Journal of Virology 73:1649-1654, 1999), and the natural product cerulenin (Lohmann V. et al., Virology 249:108-118, 1998);

(10) Antisense phosphorothioate oligodeoxynucleotides (S-ODN) complementary to sequence stretches in the 5' noncoding region (NCR) of the HCV (Alt M. et al., Hepatology 22:707-717, 1995), or nucleotides 326-348 comprising the 3' end of the NCR and nucleotides 371-388 located in the core coding region of the IICV RNA (Alt M. et al., Archives of Virology 142:589-599, 1997; Galderisi U. et al., Journal of Cellular Physiology 181:251-257, 1999);

(11) Inhibitors of IRES-dependent translation (Ikeda N et al., Agent for the prevention and treatment of hepatitis C, Japanese Patent Publication JP-08268890; Kai Y. et al. Prevention and treatment of viral diseases, Japanese Patent Publication JP-10101591);

(12) Nuclease-resistant ribozymes. (Maccjak D. J. et al., Hepatology 30 abstract 995, 1999); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

Figure 4:
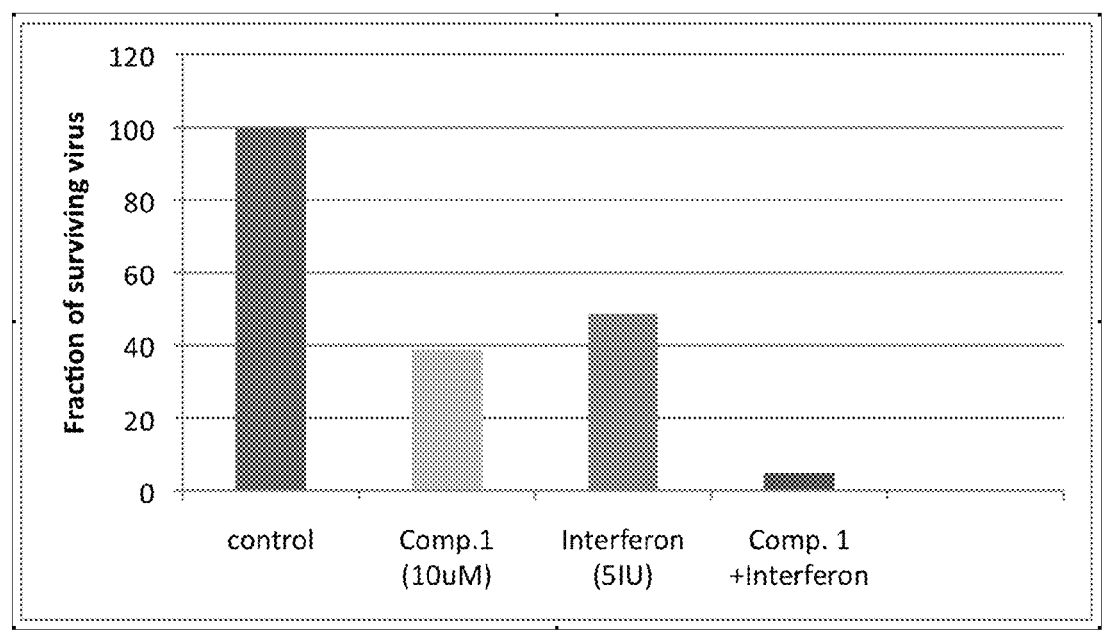
FIG. 4 is a bar graph showing synergy in the antiviral activity of Compound 1 and interferon

Surprising synergism was recorded when Compound 1 was combined with Interferon alpha. Compound shows synergistic effect with interferon-α (5 IU/well) against HCV in MDBK. MDBK cells were incubated for 6 hrs with compounds and interferon alone, or combination of compound and interferon in a 96-well plat. After 6 hrs cells were infected with $2 \times 10^4$ copies of HCV 3a genotype per well and incubated for additional 18 hrs. At the end of incubation period, total RNA was extracted by Gentra kit, and the levels of HCV RNA remaining were determined, by real time Quantitative RT-PCR assay and are shown as percentage of HCV RNA survival in cells. Results are represented as the average and standard error for three independent experiments. The results of synergy in the antiviral activity of Compound 1 and interferon shown in FIG. 4.

FIG. 4

Pharmaceutical Compositions

Hosts, including humans, infected with HCV, or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

We claim:

1. A pharmaceutical composition comprising a compound 3-amino-2-(4-nitrophenyl)-4-(3H)-quinazolinone or a pharmaceutically acceptable salt or ester thereof, in combination with one or more other antiviral agents, and one or more pharmaceutically acceptable carriers, excipients or diluents.

2. The pharmaceutical composition of claim 1, wherein the other antiviral agent is ribavirin.

3. The pharmaceutical composition of claim 1, wherein the other antiviral agent is an interferon.

4. The pharmaceutical composition of claim 1, wherein the other antiviral agents are an interferon and ribavarin.

* * * * *